United States Patent [19]

Omura et al.

[11] 4,302,381

[45] Nov. 24, 1981

[54] DENTAL MATERIAL

[75] Inventors: Ikuo Omura; Junichi Yamauchi; Yoshinori Nagase; Kyoichiro Shibatani, all of Kurashiki, Japan

[73] Assignee: Kuraray Co., Ltd., Kurashiki, Japan

[21] Appl. No.: 67,454

[22] Filed: Aug. 17, 1979

[30] Foreign Application Priority Data

Aug. 29, 1978 [JP] Japan .................................. 53-105738

[51] Int. Cl.³ .................................................. C08K 3/36
[52] U.S. Cl. ........................... 260/42.15; 260/998.11; 433/228; 526/323.1; 526/323.2; 560/224
[58] Field of Search .......................... 526/323.1, 323.2; 260/42.15

[56] References Cited

U.S. PATENT DOCUMENTS

| | | | |
|---|---|---|---|
| 3,066,112 | 11/1962 | Bowen | 260/41 |
| 3,539,533 | 11/1970 | Lee et al. | 260/47 |
| 3,547,851 | 12/1970 | Fraenglass | 526/323.1 |
| 3,751,399 | 8/1973 | Lee et al. | 260/47 UA |
| 3,926,906 | 12/1975 | Lee et al. | 260/42.53 |

Primary Examiner—Stanford M. Levin

Attorney, Agent, or Firm—Oblon, Fisher, Spivak, McClelland & Maier

[57] ABSTRACT

The present invention provides a dental material comprising a polymerizable methacrylate monomer mixture and a curing agent, said polymerizable methacrylate monomer mixture containing a compound represented by the formula

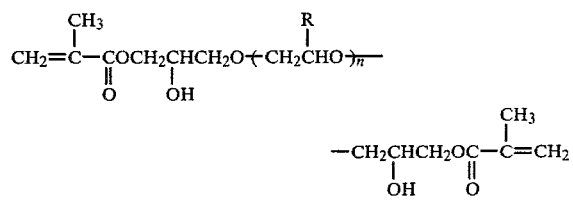

wherein R is H or methyl and n is integer of 1-4, in an amount of 5-50% by weight based on the whole polymerizable monomer mixture. Said dental material is useful as a filling material, a dental adhesive primer, and a pit and fissure sealant.

11 Claims, No Drawings

DENTAL MATERIAL

BACKGROUND OF THE INVENTION

1. Field of the Invention

The invention relates to a dental material useful as a dental filling material, a dental adhesive primer or a pit and fissure sealant, where adhesion to the teeth is strongly required. In this specification, the term "dental material" is used to include dental filling materials, dental adhesive primers, and pit and fissure sealants.

2. Description of the Prior Art

The polymerizable monomers that have so far been used in dental materials are mainly methacrylate monomers. Typical examples are, as are disclosed, for example, in U.S. Pat. Nos. 3,066,112, 3,751,399 and 3,926,906, 2,2'-bis[4-(3-methacryloxy-2-hydroxypropoxy)phenyl]-propane (hereinafter abbreviated to Bis-GMA), ethylene glycol dimethacrylate, diethylene glycol dimethacrylate, triethylene glycol dimethacrylate and tetraethylene glycol dimethacrylate, which are actually in wide use. Particularly, Bis-GMA can be used for general purposes. Since it is highly viscous, however, it is diluted with a monomer having low viscosity, such as triethylene glycol dimethacrylate.

These dental materials are required to adhere to the teeth. When the above-mentioned polymerizable monomers are polymerized and hardened on the surface of the teeth, the cured product should adhere to the tooth surface. For that reason, in the prior art dental treatment, the tooth surface is etched with an acid such as phosphoric acid. This treatment removes a smeared layer on the tooth surface and causes formation of an uneven or coarse portion or portions on the tooth surface. Now the polymerizable monomer mixture, when applied, can enter those minute depressions formed by said acid etching, whereby adhesion of the cured material to the tooth surface may be secured. With the prior art dental materials, however, adhesion is still insufficient, as can be seen from the fact that repeated application of occlusal pressure or repeated thermal expansion and contraction is apt to cause formation of gaps between the teeth and the cured product, which may lead to falling off of the filled material, unfavorable change of the teeth at the site between the teeth and the cured product (e.g. secondary caries etc). Therefore, dental materials with improved adhesion have been expected. For improved adhesion, it is essential that the polymerizable monomer mixture can enter the depressions formed by acid etching to a sufficient extent, and that the polymerizable monomer mixture is desired to be low viscosity and wettable to the teeth, to satisfy the above object.

Improved adhesion to the teeth may be achieved not only by utilizing anchor effect brought about by the above-mentioned uneven portion or portions formed on the tooth surface but also by utilizing chemical bonding with enamel and dentin. For example, certain polymerizable monomers containing phosphoric acid diester groups as disclosed in German Offenlegungsschrift No. 2,711,234.1 have good chemical affinity for the dentin, and consequently the cured products from compositions containing such monomers have been found to be excellent in adhesion to the teeth. These monomers, however, are added in small amounts in view of their characteristics, and it is necessary to use in combination with other monomer or monomers. Combined use of monomers capable of wetting the teeth easily is more effective.

SUMMARY OF THE INVENTION

Therefore, an object of the invention is to provide a dental material which is low in viscosity, is constituted by polymerizable monomers capable of wetting the teeth easily and gives a cured product with highly strong adhesion to the teeth.

Another object of the invention is to provide a dental filling material which is low in viscosity and has an excellent adhesion to the teeth.

A further object of the invention is to provide a dental adhesive primer for securing adhesion between the teeth and filling materials or orthodontic appliances.

A still further object of the invention is to provide a pit and fissure sealant which is excellent in respect of adhesion to the teeth. Other objects of the invention will be clear from the following description.

According to the present invention, the above objects can be achieved by a dental material which comprises a polymerizable methacrylate monomer mixture containing a compound (monomer A) represented by the structual formula

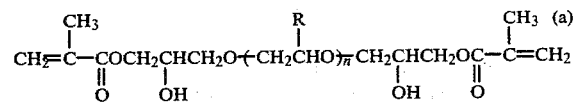

wherein R is H or methyl and n is integer of 1 through 4, in an amount of 5 to 50% by weight based on the whole polymerizable monomer mixture, and a curing agent therefor.

DETAILED DESCRIPTION OF THE INVENTION

The present invention is characterized in that monomer A is added to the prior art dental materials.

Typical examples of the compound represented by the structural formula (a) are:

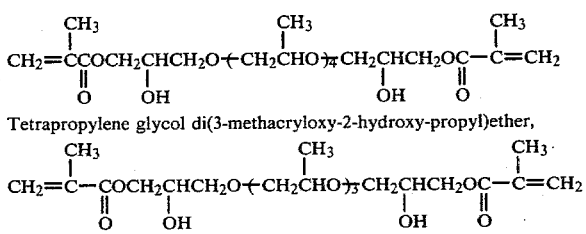

Tetrapropylene glycol di(3-methacryloxy-2-hydroxy-propyl)ether,

Tripropylene glycol di(3-methacryloxy-2-hydroxy-propyl)ether

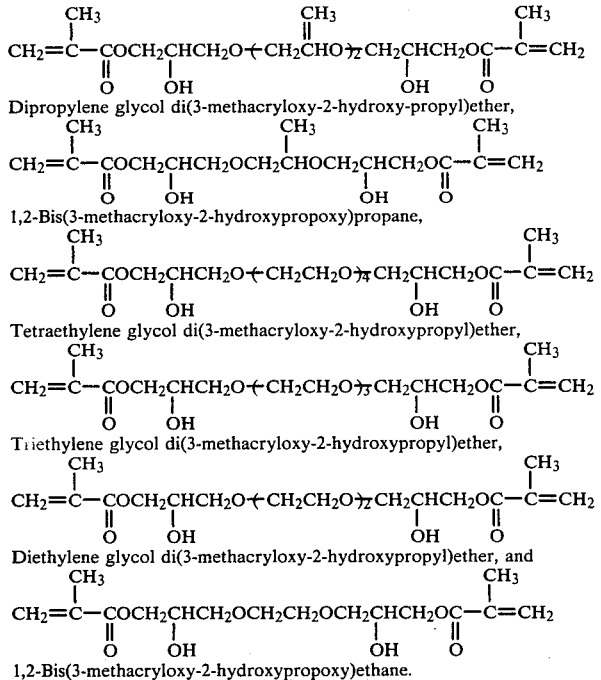
Dipropylene glycol di(3-methacryloxy-2-hydroxy-propyl)ether, 1,2-Bis(3-methacryloxy-2-hydroxypropoxy)propane, Tetraethylene glycol di(3-methacryloxy-2-hydroxypropyl)ether, Triethylene glycol di(3-methacryloxy-2-hydroxypropyl)ether, Diethylene glycol di(3-methacryloxy-2-hydroxypropyl)ether, and 1,2-Bis(3-methacryloxy-2-hydroxypropoxy)ethane.

Among these, those compounds of formula (a) wherein R is hydrogen atom are preferred because they are superior in the effect to be described later to those compounds of formula (a) wherein R is methyl group. Particularly, 1,2-Bis(3-methacryloxy-2-hydroxypropoxy)ethane (n−1) is preferred. The compounds of formula (a) can be prepared in a manner easy to those skilled in the art by reacting a compound of the formula.

  (b)

with epichlorohydrin in the presence of an alkali and then reacting the resulting diglycidyl ether with methacrylic acid. In cases where n is 1, they may be produced by reacting ethylene (or propylene) glycol diglycidyl ether with methacrylic acid in a slight excess. 1,2-Bis(3-methacryloxy-2-hydroxypropoxy) ethane is commercially available. It has been found that the use of such a monomer as mentioned above as a component of the polymerizable methacrylate monomer mixture in an amount of 5–50% by weight based on the whole polymerizable methacrylate monomer mixture can remarkably improve adhesion of the cured product to the teeth. With amounts less than 5% by weight, the improvement in adhesion is slight, and, with amounts exceeding 50% by weight, increase of the water absorbing power of the cured product results, which may lead to depression of the mechanical strength.

Such an effect as mentioned above is thought to be due to improvement in the ability of the polymerizable monomer mixture to wet the dentin, which is attributable to the fact that the monomer mentioned above, i.e. the compound of formula (a), has a low viscosity and to the presence of the two hydrophilic hydroxyl groups in its molecule. Said monomer can easily copolymerize with the methacrylate monomers used in the conventional dental materials, such as Bis-GMA and triethylene glycol dimethacrylate, and, because of its bifunctionality, the amount of elutable matter in the cured product is remarkably small as compared with the case of a monofunctional hydrophilic monomer such as 2-hydroxyethyl methacrylate. Since the monomer is an ester derived from an epoxy compound with a high molecular weight, the use of this compound can render the contraction of the cured product on polymerization relatively small, and therefore the dental material of the present invention can be used with advantage as dental filling material where contraction due to polymerization during hardening, i.e. curing, is a problem. Said compound is chemically stable and is excellent in shelf life. Although a compound having two hydroxyl groups in its molecule and having the structural formula

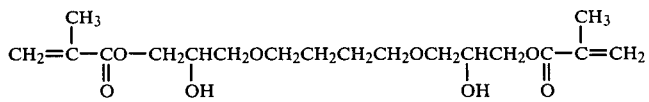

namely, 1,4-bis(3-methacryloxy-2-hydroxypropoxy)butane, is known, from U.S. Pat. No. 3,751,399, to be usable in dental materials, such a compound cannot produce a sufficient effect in improving adhesion to the teeth, as shown in an example for comparison to be described later.

Those polymerizable methacrylate monomers that have been used in conventional dental materials may also be used in combination with monomer A according to the invention. Such polymerizable methacrylate monomers contain each 5-40 carbon atoms and include monomethacrylates such as methyl methacrylate and butyl methacrylate, as well as polyfunctional (bi- to tetra-functional) methacrylate monomers to be mentioned later. Especially, from the viewpoints of hardness and water resistance, polyfunctional methacrylates are preferred, and polyfunctional methacrylates containing aromatic rings, among others, are particularly preferred. Such methacrylates which contain aromatic rings are, for example, besides the Bis-GMA mentioned above, 2,2'-bis(4-methacryloxyphenyl)propane, 2,2'-bis(4-methacryloxyethoxyphenyl)propane, 2,2'-bis(4-methacryloxyethoxyethoxyphenyl)propane, 2,2'-bis(4-methacryloxypropoxyphenyl)-propane and various aromatic-ring-containing methacrylates as disclosed in U.S. Pat. No. 3,751,399 cited above. These may be used either alone or in combination. In the prior art dental materials, Bis-GMA is widely used which gives a cured product with good chemical and mechanical properties. In practicing the invention, too, it is preferable to use Bis-GMA (also called sometimes herein monomer B) together with monomer A. From the viewpoint of mechanical strength of the cured product, it is suitable that the amount of the aromatic-ring-containing methacrylate, such as Bis-GMA, in the polymerizable methacrylate monomer mixture is, depending upon the use of the dental material, in the range of 20–80% by weight based on the whole polymerizable monomer mixture. When the polymerizable monomers are used, as will be later described, as binders for fillers, relatively large amounts of Bis-GMA are preferable, such as 40–70% by weight, from the viewpoint of chemical and mechanical properties. In the pit and fissure sealants or adhesive primers, the amount of Bis-GMA is preferably 50% by weight or less so as to give low viscosity compositions, which can easily be applied to the teeth.

In practicing the invention, it is preferable to add, besides the above-mentioned monomers A and B, neopentyl glycol dimethacrylate (monomer C), in an amount of 0.5–2 parts by weight per part by weight of monomer A. The monomer C becomes a hydrophobic component in the cured product and, when added in such an amount as mentioned above, depresses that water absorbing power of the cured product which monomer A brings about, so that the water resistance of the cured product can be maintained. The use of neopentyl glycol dimethacrylate is particularly effective, as compared with many hydrophobic monomers such as 1,2-propanediol dimethacrylate, 1,3-propanediol dimethacrylate, 1,4-butanediol dimethacrylate and 1,6 hexanediol dimethacrylate.

Generally, since Bis-GMA is very viscous at room temperature, it is difficult to use the same alone and therefore it is usually diluted with a dimethacrylate (monomer D) represented by the structural formula

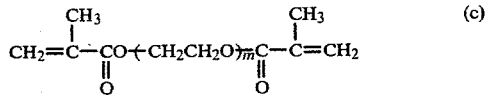

wherein m is integer of 1 through 4, and having a low viscosity, so as to adjust the viscosity. According to the invention, the use of monomer D is not essential because monomer A has a low viscosity. However, monomer D may be used as one component of the polymerizable methacrylate monomer mixture for the purpose of adjusting the viscosity of dental materials. When the binder for a filler is composed of monomers A, B and C mentioned above, and if necessary, monomer D may further be added to give a filling material with a low viscosity, in an amount of not more than 25% by weight based on the monomer B plus the monomer D. With amounts exceeding 25% by weight, the balance of the various properties for the dental material, such as the adhesion to the tooth, the mechanical strength and the water absorption becomes undesirable, because the amounts of the monomers A, B and C are relatively decreased. Monomer D includes ethylene glycol dimethacrylate, diethylene glycol dimethacrylate, triethylene glycol dimethacrylate and tetraethylene glycol tetramethacrylate.

For polymerization and hardening of the polymerizable methacrylate monomer mixture on the tooth surface or in the tooth cavity, the dental material of the invention, as is usual in the art, contains a curing agent. Generally, the curing agent is of the room temperature cure type and consists of a catalyst and an activator. A suitable catalyst is benzoyl peroxide, and a suitable activator is a tertiary amine, such as N,N-dimethyl-p-toluidine or N,N-di(2-hydroxyethyl)-p-toluidine. Such a curing agent or system is added in an amount of 0.1–6% by weight based on the polymerizable monomer mixture. With such a curing system, the polymerizable methacrylate monomers in the composition can be polymerized substantially completely. In cases where such an agent causing polymerization and hardening is used, the dental material of the invention is, as is the case with composite resin compositions available in the market from the shelf life standpoint, supplied to dentists, who are the users, as an at least two part package so that the catalyst and the activator can be separately packed, and the parts are mixed prior to use to give a contemplated composition. The constituents of the dental material are divided in an appropriate manner and packed in the respective package parts in consideration of shelf life thereof, as will be described later. A photosensitizer may also be used as the curing agent, and in this case one part packaging is possible, and the composite resin system, after filling into the cavity, can be cured by exposure to or irradiation of ultraviolet or visible rays. Usable photosensitizers are benzoin methyl ether, benzoin ethyl ether, p-benzoylbenzyl bromide and so forth. The photosensitizer is formulated generally in an amount of 0.01–10% by weight based on the polymerizable monomer mixture.

The dental material of the invention, owing to its containing monomer A, is excellent in adhesion of the cured product to the teeth. Therefore, the dental material of the present invention is used as a dental filling material, a dental adhesive primer or a pit and fissure sealant, where adhesion to the teeth is required. Thus, the addition of monomer A to the filling material makes the filling material in paste form less viscous and causes increase in flowability thereof, so that the material can fill every nook and corner of the tooth cavity having a complicated shape, and at the same time, because such a monomer wets the teeth well, good adhesion results between the filled and cured material and the teeth, showing an excellent margin sealing property thereof. Furthermore, when, in applying the filling material into the tooth cavity, monomer A is added to the pretreating agent (adhesive primer) for applying to the tooth surface, the pretreating agent can wet both the teeth and the filling material to sufficient extent such that no small air layers or no bubbles can remain. While the pretreating agent is cured together with the filling material by the action of the curing agent, the interaction between the teeth and monomer A is so strong that even after the curing the resin keeps a good adhesion to the teeth, showing its excellent margin sealing property. When monomer A is added to a methacrylate-type pit and fissure sealant, improved penetration of the cured product into pit and fissures and consequently improved adhesion of the cured product to the etched enamel can be obtained. In particular, the filling material which contains monomer A can be a low-viscosity-type filling material as compared with the commercially available filling materials, and therefore the range of application of the filling material can be widened. Detailedly, the composite resins now on the market, when the constituents thereof are mixed, give pastes having such high viscosities as $1.0 \times 10^4$ poises or higher, and therefore it is difficult to apply such pastes to milk teeth which have small cavities. On the contrary, the filling material of the present invention can be made into a paste having a viscosity in the range of $2.0 \times 10^2$ to $5.0 \times 10^3$ poises by appropriately selecting and adjusting the kinds and amounts of the components of the polymerizable methacrylate monomer mixture and of the filler as described later, and now it is easy to apply the filling material to the cavity of the milk teeth.

In cases where the dental material of the invention is to be used as a filling material (especially a composite filling material), a filler in powder form is further added as a constituent. Thus, the filling material consists essentially of a polymerizable methacrylate monomer mixture, a filler and a curing agent, and these constituents are mixed to a paste, which is injected into the tooth cavity and cured. The polymerizable methacrylate monomers, on polymerization caused by the curing agent, become a binder for the filler. Details of the polymerizable methacrylate monomer mixture and the curing agent to be used in the filling material are as above mentioned.

Further, when the amount of Bis-GMA which is one constituent of the polymerizable monomer mixture is relatively small and the amounts of such low viscosity polymerizable monomers as monomer A, monomer C and monomer D are relatively large, the resulting filling material of the invention is a low viscosity type. It has been found that the following composition of the polymerizable monomer mixture is very desirable for the filling material of the low viscosity type. It consists essentially of monomer A in amount of 10–20% by weight, monomer B in amount of 51–60% by weight, monomer C in amount of 10–20% by weight, and monomer D in amount of 10–17% by weight of the whole monomer mixture. The dental filling material containing such a polymerizable monomer mixture has good mechanical properties and an excellent adhesion to tooth, in addition to a low viscosity.

According to this invention, it is preferable that the amount of the polymerizable methacrylate monomer mixture is 30–50% by volume and that of the filler 70–50% by volume, each based on the composition consisting of the polymerizable methacrylate monomer mixture and the filler. When the polymerizable monomer mixture amounts to less than 30% by volume, the flowability of the paste is poor, and when said monomer mixture amounts to more than 50% by volume, shrinkage on cure is excessive and the cured material shows a performance poor in physical and mechanical properties (e.g. compressive strength, hardness, coefficient of thermal expansion). Preferred fillers are inorganic fillers having low coefficients of thermal expansion and surface-treated with silane coupling agents, such as silanated glass or quartz powder having particle sizes of 100 microns or less. It is preferable in practicing the invention to add as part of said filler hydrophilic colloidal silica which is finely divided anhydrous silica having an area-average particle size of 5–50 millimicrons and having on the surface thereof silanol (Si-OH) groups at a density of 2–3 per 100 square Angstroms. A fine powder of an organic macromolecular compound containing such as inorganic material as mentioned above may also be used as the filler. In the case of the dental filling material having a low viscosity, when the paste composition consisting of the polymerizable monomer mixture and the filler is stored for long, the filler shows a tendency toward precipitation. The addition of the above-mentioned hydrophilic colloidal silica is effective in preventing such a precipitation. Preferably, it is added in an amount of 0.5–20% by volume based on the polymerizable monomer mixture plus the filler. As soon as both the catalyst and the activator are added to the filling material of the invention, curing starts, and therefore the constituents are packed as an at least two part package, as mentioned previously. When the contents of the package parts are mixed prior to use, there is obtained a paste-like composition in which the constituents are present each in the specified amount. The package form may be either that of the paste-catalyst type which consists of one package containing the paste consisting of the polymerizable monomer mixture, filler and activator and the other package containing the catalyst alone (the catalyst may be diluted with an appropriate extender), or that of the two paste type which consists of two packages each containing the paste divided into two portions and consisting of the polymerizable monomer mixture and filler, one package further containing the catalyst and the other the activator. In filling the tooth cavity with the filling material of the invention, it is preferable to first treat the tooth surface with an acid etching agent e.g. comprising phosphoric acid and then apply an adhesive primer comprising a polymerizable monomer system and a curing agent. The polymerizable monomer system of the adhesive primer may be any of the above mentioned monomers A, B, C and D and other various polymerizable methacrylate monomers such as the phosphoric acid diester group-containing methacrylate, or any combination thereof. These monomers are mixed with a conventional curing agent of the room temperature cure type and then applied thinly to the cavity surface, and thereafter the filling material is introduced. For convenience sake, therefore, the filling material and the adhesive primer are combined and supplied as a dental restorative system to dentists.

As previously mentioned, the dental material of the present invention can be used also as a dental adhesive primer or as a pit and fissure sealant. In such a case, the dental material is composed of a polymerizable methacrylate monomer mixture and a curing agent, and, as mentioned above, monomer A is used as one of the polymerizable methacrylate monomers. In addition to monomer A, various polymerizable methacrylate monomers such as mentioned previously can be used. Among others, however, Bis-GMA, ethylene glycol dimethacrylate, diethylene glycol dimethacrylate, triethylene glycol dimethacrylate and neopentyl glycol dimethacrylate, and mixtures thereof are preferred.

Especially, Bis-GMA is most generally used. It is preferable to add a polymerizable methacrylate monomer having an ability of chemically adhering to the dentin, such as 2-methacryloxyphenyl hydrogen phosphate, because such a monomer adds an effect of chemical adhesion to the effect of monomer A. The curing agent is, as mentioned above, a curing agent of the room temperature cure type which consists of a catalyst and an activator, such as a benzoyl peroxide-amine, sulfinate-acid or benzoyl peroxide-amine-sulfinate salt system, or a photosensitizer. If necessary, an inorganic filler such as glass or quartz powder or an organic filler such as polymethyl methacrylate powder may be added to the above constituents. The adhesive primer of the invention which contains monomer A is effective in securing adhesion between the teeth and the filling material, and is combined with a usual filling material and supplied to dentists in the form of a dental restorative system. The adhesive primer is also useful for securing adhesion between the teeth and an orthodontic appliance.

As can be understood from the foregoing, the presence of monomer A in the filling material, adhesive primer or pit and fissure sealant brings about marked improvement in adhesiveness of such dental material to the teeth, and as a result falling off of the cured filling material or unfavorable change of the teeth at the sites between the teeth and the cured material does not occur and the original treated state can be maintained for a long period of time. The dental materials containing monomer A are not toxic to the human.

The present invention will be more fully illustrated by the following examples, which, however, by no means restrict the invention.

EXAMPLE 1

Paste (A) and paste (B) were prepared according to the following recipes:

| Paste (A): | Parts by weight |
|---|---|
| Bis-GMA | 13.8 |
| Triethylene glycol dimethacrylate | 4.2 |
| Neopentyl glycol dimethacrylate | 3.5 |
| 1,2-Bis(3-methacryloxy-2-hydroxy-propoxy) ethane | 3.5 |
| Silanated quartz powder (particle sizes less than 60 microns) | 73.2 |
| Hydrophilic colloidal silica* | 1.5 |
| N,N-Di(2-hydroxyethyl)-p-toluidine | 0.25 |

*"Aerosil 380", manufactured by Japan Aerosil K.K.

| Paste (B): | Parts by weight |
|---|---|
| Bis-GMA | 13.8 |
| Triethylene glycol dimethacrylate | 4.2 |
| Neopentyl glycol dimethacrylate | 3.5 |
| 1,2-Bis(3-methacryloxy-2-hydroxypropoxy)-ethane | 3.5 |
| Silanated quartz powder (as above) | 73.2 |
| Hydrophilic colloidal silica (as above) | 1.5 |
| Benzoyl peroxide | 0.5 |

(The filler amounts to 56% by volume of the polymerizable monomers plus the filler.)

One or two cavities, 2 mm wide, 4 mm long and 2 mm deep, were prepared on the side of the crown of a human tooth by means of a diamond bar. Four cavities in all were thus prepared. The enamel of each cavity was treated with an etching agent containing 40% phosphoric acid for a minute. Then the cavities were washed with water and dried using an air syringe, and a bonding agent containing a methacrylate monomer having a phosphoric acid ester group was applied to the cavities. The volatile ethanol in the bonding agent was evaporated again using an air syringe. Equal amounts of paste (A) and paste (B) were mixed for 30 seconds and the cavities were filled with the paste mixture. Five minutes after the filling, the teeth were immersed in water. An hour later, the whole of each tooth, except for the filled portion, was fortified with a resin, and allowed to stand in water at 37° C. for 24 hours. Thereafter, the overfilled filling material was removed by means of a #500 emery paper. Then the teeth were immersed 100 times in a fuchsine-colored water at 5° C. and in a fuchsine colored water at 60° C. alternately at one-minute intervals. Each sample obtained was sliced with a cutter to prepare 4 thin sections. The 16 (4×4) sections were evaluated for the degree of penetration of the fuchsine into the adhesion interface by a scoring method. The degree of penetration was 9.0%. The results is very excellent when compared with the result obtained in the example for comparison described below.

The degree of fuchsine penetration is determined as follows: On a thin section specimen obtained by slicing the filled tooth, there are two interfaces between the tooth and the filling material where the dye could penetrate (on both ends of the filling material). For each of the two interfaces, dye penetration to the enamel is scored as 5%, to the dentin as 30% and to the cavity bottom as 50%. The scores for both the interfaces added together give the degree of dye penetration for that specimen. The result of the dye penetration test is expressed in terms of the mean value of 16 evaluations.

Further, the viscosity of paste (A) or paste (B), which was measured with Weissenberg-Rheogoniometer (made by Sungamo Weston Controls Ltd.) at 25° C. and the shear rate of 1.35 sec$^{-1}$, was $1.1 \times 10^3$ poise, respectively. This value shows that it is possible to apply this filling material to the cavity of the milk teeth.

EXAMPLE FOR COMPARISON 1

Paste (C) and paste (D) were prepared according to the following recipes:

| Paste (C): | Parts by weight |
|---|---|
| Bis-GMA | 13.8 |
| Triethylene glycol dimethacrylate | 11.2 |
| Silanated quartz powder (as in Example 1) | 73.2 |
| Hydrophilic colloidal silica (as in Example 1) | 1.5 |
| N,N-Di(2-hydroxyethyl)-p-toluidine | 0.25 |

| Paste (D): | Parts by weight |
|---|---|
| Bis-GMA | 13.8 |
| Triethylene glycol dimethacrylate | 11.2 |
| Silanated quartz powder (as above) | 73.2 |
| Colloidal silica (as above) | 1.5 |
| Benzoyl peroxide | 0.5 |

The tooth cavities were filled with the intimate mixture of paste (C) and paste (D) according to the procedure of Example 1, and the dye penetration test was performed. The dye penetration degree as evaluated by the same method as employed in Example 1 was 22.6%. Since it has been revealed from Example 2 as described later that the addition of neopentyl glycol dimethacrylate has a tendency to make the composite resin hydrophobic and does not cause increase in adhesion strength, it is clear from the comparison of the result in Example 1 and that in Example for Comparison 1 that 1,2-bis(3-methacryloxy-2-hydroxypropxy)ethane, that is a compound of structural formula (a) where R is H and n is 1, has an effect of improving the adhesion strength.

EXAMPLE FOR COMPARISON 2

Paste (E) and paste (F) were prepared according to the recipes for paste (A) and paste (B) in Example 1, except that the same amounts of 1,2-bis(3-methacryloxy-2-hydroxypropoxy)-butane disclosed in U.S. Pat. No. 3,751,399 were used in place of 1,2-bis(3-methacryloxy-2-hydroxypropoxy)ethane. Paste (E) and paste (F) were mixed and applied to the teeth by the procedure of Example 1, and the dye penetration degree was evaluated. The degree of fuchsine penetration was 17.2%. This result shows that monomer A used in accordance with the present invention is much superior in the effect in question to 1,2-bis(3-methacryloxy-2-hydroxypropoxy)butane described in said U.S. patent.

EXAMPLE FOR COMPARISON 3

Pastes (G) and (H) were prepared according to the following recipes:

| Paste (G): | Parts by weight |
|---|---|
| Bis-GMA | 13.8 |
| Triethylene glycol dimethacrylate | 10.1 |
| 1,2-Bis(3-methacryloxy-2-hydroxypropoxy)-ethane | 1.1 |
| Silane-treated quartz powder (as in Example 1) | 73.2 |
| Colloidal silica (as in Example 1) | 1.5 |
| N,N-Di(2-hydroxyethyl)-p-toluidine | 0.25 |

| Paste (H): | Parts by weight |
|---|---|
| Bis-GMA | 13.8 |
| Triethylene glycol dimethacrylate | 10.1 |
| 1,2-Bis(3-methacryloxy-3-hydroxypropoxy)-ethane | 1.1 |
| Silane-treated quartz powder (as in Example 1) | 73.2 |
| Colloidal silica (as in Example 1) | 1.5 |
| Benzoyl peroxide | 0.5 |

Using pastes (G) and (H) and proceeding as in Example 1, the teeth were filled and the dye penetration degree was evaluated. The fuchsine penetration degree was 16.5%. This result shows that, when the monomer A content is about 4.4.% by weight, that is outside the range specified according to the invention, its effect of improving margin sealing property is only slight.

EXAMPLE FOR COMPARISON 4

Paste (I) and paste (J) were prepared according to the following recipes:

| Paste (I): | Parts by weight |
|---|---|
| Bis-GMA | 8 |
| 1,2-Bis(3-methacryloxy-2-hydroxypropoxy)-ethane | 17 |
| Silanated quartz powder (as in Example 1) | 73.2 |
| Colloidal silica (as in Example 1) | 1.5 |
| N,N-Di(2-hydroxyethyl)-p-toluidine | 0.25 |

| Paste (J): | Parts by weight |
|---|---|
| Bis-GMA | 8 |
| 1,2-Bis(3-methacryloxy-2-hydroxypropoxy)-ethane | 17 |
| Silanated quartz powder (as in Example 1) | 73.2 |
| Colloidal silica (as in Example 1) | 1.5 |
| Benzoyl peroxide | 0.5 |

Equal amounts of pastes (I) and (J) were mixed, and cured into a disk, 35 mm in diameter and 1 mm thick. The disk was warmed at 37° C. for 24 hours, weighed, and then immersed in water at 37° C. One month later, the weight increase for this disk was measured, and the percent water absorption calculated. This was 2.8% by weight. The percent water absorption determined by this procedure for the disk prepared from pastes (A) and (B) of Example 1 was 1.2% by weight. Comparison of both the results teaches that monomer A contents exceeding the upper limit of the range specified according to the invention undersirably result in increase in water absorbing power of the cured material.

EXAMPLE 2

Paste (K) and paste (L) were prepared in the same manner as Example 1, except that triethylene glycol dimethacrylate was further added in place of neopentyl glycol dimethacrylate. The total amount of triethylene glycol dimethacrylate was 7.7 parts by weight.

The tooth cavities were filled with the mixture of paste (K) and paste (L) according to the procedure of Example 1, and the dye penetration test was performed. The dye penetration degree was 8.0%, which is similar to that of Example 1.

Incidentally, the percent water absorption determined with the procedure as described in Example for comparison 4 was 1.8% by weight. This value was considerably greater than that of the cured resin in Example 1, which was 1.2% by weight. This result shows that the addition of neopentyl glycol dimethacrylate makes the cured resin hydrophobic, and the presence of both the components, that is, 1,2-bis(3-methacryloxy-2-hydroxypropoxy) ethane and neopentyl glycol dimethacrylate in the dental filling material is very preferable, because the balance of the properties between the adhesion to tooth and the water absorption is kept.

EXAMPLE 3

Paste (M) and paste (N) were prepared according to the following recipes.

| Paste (M): | Parts by weight |
|---|---|
| Bis-GMA | 13.8 |
| Triethylene glycol dimethacrylate | 6.2 |
| Neopentyl glycol dimethacrylate | 2.5 |
| 1,2-Bis(3-methacryloxy-2-hydroxy-propoxy)-ethane | 2.5 |
| Silanated quartz powder (as in Example 1) | 73.2 |
| Hydrophilic colloidal silica (as in Example 1) | 1.5 |
| N,N-Di(2-hydroxyethyl)-p-toluidine | 0.25 |

| Paste (N): | Parts by weight |
|---|---|
| Bis-GMA | 13.8 |
| Triethylene glycol dimethacrylate | 6.2 |
| Neopentyl glycol dimethacrylate | 2.5 |

| Paste (N): | Parts by weight |
|---|---|
| 1,2-Bis(3-methacryloxy-2-hydroxy-propoxy)-ethane | 2.5 |
| Silanated quartz powder (as above) | 73.2 |
| Hydrophilic colloidal silica (as above) | 1.5 |
| Benzoyl peroxide | 0.5 |

The tooth cavities were filled with the intimate mixture of paste (M) and paste (N) according to the procedure of Example 1, and the dye penetration test was performed. The dye penetration degree was 12%. This result is excellent as compared with the result in the Examples for comparison described above.

Incidentally, when the amount of trimethylene glycol dimethacrylate is 31% by weight based on Bis-GMA plus triethylene glycol dimethacrylate as in this Example, the adhesion strength to the tooth is slightly decreased as compared with that of Example 1, because the content of 1,2-bis(3-methacryloxy-2-hydroxypropoxy)ethane is relatively reduced.

EXAMPLE 4

A filling material of the paste-catalyst type was prepared according to the following recipes:

| Paste (O): | Parts by weight |
|---|---|
| Bis-GMA | 13.8 |
| Triethylene glycol dimethacrylate | 4.2 |
| Neopentyl glycol dimethacrylate | 3.5 |
| 1,2-Bis(3-methacryloxy-2-hydroxypropoxy)-ethane | 3.5 |
| Silanated quartz powder (as in Example 1) | 73.3 |
| Hydrophilic colloidal silica (as in Example 1) | 1.5 |
| N,N-Diethanol-p-toluidine | 0.2 |

| Paste (P) | Parts by weight |
|---|---|
| Dibutyl phthalate | 25 |
| Silanated quartz powder (as above) | 69 |
| Hydrophilic colloidal silica (as above) | 2 |
| Benzoyl peroxide | 4 |

The quartz powder used was, as in Example 1, a powder with a particle size of 60 microns or less, the surface of which had been treated wiht a silane coupling agent. The hydrophilic colloidal silica was, as in Example 1, Aerosil 380, which was a fine particle anhydrous silica. The mixture resulting from paste (O) and paste (P) in a ratio of 30:1 by weight contained 56% by volume of the filler, which consisted of the quartz powder and the hydrophilic colloidal silica, based on the polymerizable monomers plus the filler. The amount of the hydrophilic colloidal silica was 1.8% by volume. An adhesive primer having the following composition was prepared. Thus, a dental restorative system was composed of the above filling material and this adhesive primer.

| Primer (Q): | Parts by weight |
|---|---|
| Ethanol | 100 |
| Sodium benzenesulfinate | 3 |
| N,N-Di(2-hydroxyethyl)-p-toluidine | 1.5 |

| Primer (R): | Parts by weight |
|---|---|
| Bis-GMA | 25 |
| Neopenthyl glycol dimethacrylate | 25 |
| 1,2-Bis(3-methacryloxy-2-hydroxypropoxy)-ethane | 40 |
| 2-Methacryloxyphenyl hydrogen phosphate | 10 |
| Benzoyl peroxide | 2 |
| 2,6-Di-tert-butyl-p-cresol | 0.03 |

A human tooth was treated with this restorative system in the following manner. First, the whole Class V cavity of a fore-tooth was etched with 40% aqueous phosphoric acid for one minute and then air-dried sufficiently. Then a 1:1 mixed solution of primer (Q) and primer (R) was applied to the whole cavity surface and the ethanol was evaporated by air blowing. The cavity was filled with a mixture of paste (O) and paste (P) in a ratio of 30:1 by weight by the conventional use of a syringe. One day after the filling, the surface was finished by polishing. One week after the filling, a percolation test for the filled tooth was conducted by the procedure of Example 1. Any marginal leakage could not be observed. The filling material and the cavity wall were in perfect adhesion, and any formation of gaps was not observed, either.

Past (O) could be stored in a polypropylene syringe 13 mm in inner diameter at room temperature for a year without any change. Precipitation of the filler did not occur. The above package form is therefore a satisfactory one.

What is claimed is:

1. A dental filling material, which comprises:
   (1) a polymerizable methacrylate monomer mixture consisting essentially of a compound of the formula:

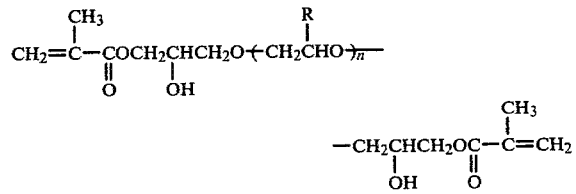

wherein R is hydrogen or methyl and n is an integer of 1 to 4 and at least one polymerizable methacrylate comonomer having from 5 to 40 carbon atoms, said compound being present in said monomer mixture in an amount of 5–50% by weight and said comonomer being present in said mixture in an amount of 95–50% by weight, the percentages being based upon the total weight of polymerizable methacrylate monomers in the monomer mixture; (2) a curing agent and (3) a powdered filler.

2. The dental filling material of claim 1, wherein R in said formula is hydrogen.

3. The dental filling material of claim 2, wherein n in said formula has a value of 1.

4. The dental filling material of claim 3, wherein one of said comonomers (B) is (B') an aromatic ring containing polyfunctional methacrylate monomer, the amount of said monomer component (B') ranging from 20–80% by weight of the polymerizable methacrylate monomer mixture.

5. The dental filling material of claim 4, wherein said monomer (B') is 2, 2'-bis [4-(3-methacryloxy-2-hydroxypropoxy) phenyl] propane.

6. The dental filling material of claim 5, wherein said comonomer component (B) comprises neopentyl glycol dimethacrylate and 2, 2'-bis [4-(3-methacryloxy-2-hydroxypropoxy) phenyl] propane, said neopentyl glycol dimethacrylate being present in an amount of 0.5–2 parts by weight per part by weight of said component (A).

7. The dental filling material of claim 6, wherein said comonomer component (B) comprises a mixture of 2, 2'-bis [4-(3-methacryloxy-2-hydroxypropoxy) phenyl] propane, neopentyl glycol dimethacrylate and a compound (C) of the formula:

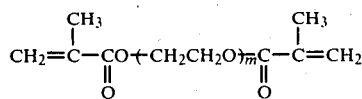

wherein m is an integer of 1 to 4, said compound (C) being present in an amount of not more than 25% by weight based on the amount of the said compound (C) and 2, 2'-bis [4-(3-methacryloxy-2-hydroxypropoxy) phenyl] propane.

8. The dental filling material of claim 7, wherein said compound (C) is triethylene glycol dimethacrylate.

9. The dental filling material of claim 1, wherein said curing agent is a room temperature curing system consisting of a catalyst and an activator therefor.

10. A dental filling material, which comprises: (1) a monomer mixture of (a) 1, 2-bis-(3-methacryloxy-2-hydroxypropoxy) ethane, (b) 2, 2'-bis-[4-(3-methacryloxy-2-hydroxypropoxy) phenyl] propane, (c) neopentyl glycol dimethacrylate, and (d) triethylene glycol dimethacrylate, the amounts of components (a), (b), (c), and (d) in the total monomer mixture being 10–20% by weight, 51–60% by weight, 10–20% by weight and 10–17% by weight respectively; (2) a curing agent and (3) a powdered filler.

11. The dental filling material of claim 10, wherein said polymerizable methacrylate monomer mixture (1) and said powdered filler are present in said dental filling material in amounts ranging from 30–50% by volume and 70–50% by volume respectively, the respective volume percentages being based upon the total volume of monomer mixture and filler.

* * * * *

UNITED STATES PATENT AND TRADEMARK OFFICE
CERTIFICATE OF CORRECTION

PATENT NO. : 4,302,381
DATED : November 24, 1981
INVENTOR(S) : Ikuo Omura et al

It is certified that error appears in the above—identified patent and that said Letters Patent is hereby corrected as shown below:

Column 3, line 1, omit entire line 1 and insert

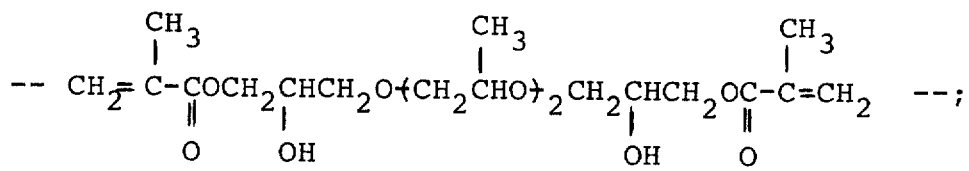

Column 3, line 35, change "(n-1)" to --(n=1)--;

Column 9, line 8, change "sulfinate" to --sulfinic--;

Column 11, line 41, change "1,2-Bis(3-methacryloxy-3-hydroxy-propoxy)-" to --1,2-Bis(3-methacryloxy-2-hydroxypropoxy)- --;

Column 14, line 28, change "Past" to --Paste--;

line 37, after "mula" insert --(A)--;

UNITED STATES PATENT AND TRADEMARK OFFICE
CERTIFICATE OF CORRECTION

PATENT NO. : 4,302,381

DATED : November 24, 1981

INVENTOR(S) : Ikuo Omura et al

It is certified that error appears in the above—identified patent and that said Letters Patent is hereby corrected as shown below:

Column 14,  line 49, after "and" insert --(B)--;

line 51, after "pound" insert --(A)--;

line 53, after "comonomer" insert --(B)--.

Signed and Sealed this

Twenty-second Day of June 1982

[SEAL]

*Attest:*

GERALD J. MOSSINGHOFF

*Attesting Officer*    *Commissioner of Patents and Trademarks*